United States Patent
Sun et al.

(10) Patent No.: US 8,247,625 B2
(45) Date of Patent: Aug. 21, 2012

(54) CATALYTIC ADDITION OF HYDROFLUOROCARBONS TO FLUOROOLEFINS

(75) Inventors: Xuehui Sun, Swedesboro, NJ (US); Viacheslav A. Petrov, Hockessin, DE (US); Mario Joseph Nappa, Newark, DE (US); Velliyur Nott Mallikarjuna Rao, Wilmington, DE (US); Ekaterina N. Swearingen, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 352 days.

(21) Appl. No.: 12/307,754

(22) PCT Filed: Jul. 3, 2007

(86) PCT No.: PCT/US2007/015467
§ 371 (c)(1),
(2), (4) Date: Mar. 8, 2009

(87) PCT Pub. No.: WO2008/008252
PCT Pub. Date: Jan. 17, 2008

(65) Prior Publication Data
US 2009/0299108 A1 Dec. 3, 2009

Related U.S. Application Data

(60) Provisional application No. 60/819,150, filed on Jul. 7, 2006.

(51) Int. Cl.
C07C 17/266 (2006.01)
C07C 17/26 (2006.01)
(52) U.S. Cl. ........................................ 570/172; 570/171
(58) Field of Classification Search .................. 570/171, 570/172
See application file for complete search history.

(56) References Cited

U.S. PATENT DOCUMENTS

| | | | | |
|---|---|---|---|---|
| 5,227,547 | A | * | 7/1993 | Ohnishi et al. ................. 570/172 |
| 6,184,426 | B1 | * | 2/2001 | Belen'Kill et al. ............ 570/172 |
| 2006/0106263 | A1 | | 5/2006 | Miller |

OTHER PUBLICATIONS

Andrea Oberhauser, Examining Division, European Patent Office, Minutes of Oral Proceedings Sent in Accordance With Rule 124(4) EPC, Jan. 2012.
Franck Bertrand et al, Examining Division, Decision From the Oral Proceedings Dated Jan. 12, 2012, Dated Feb. 1, 2012.

* cited by examiner

*Primary Examiner* — Jafar Parsa

(57) ABSTRACT

A process is disclosed for making $RR^1R^2CCR^1R^2F$ wherein R is selected from the group consisting of $CH_3$, $CH_2F$, $C_2H_4F$, and $F(CF_2)_nCH_2CH_2$ where n is an integer from 1 to 10, each $R^1$ is independently selected from the group consisting of H, Cl, F and $CF_3$, and each $R^2$ is independently selected from the group consisting of H, F and $CF_3$. The process involves reacting RF with $R^1R^2C=CR^1R^2$ in the presence of $SbF_5$ to produce a product mixture comprising $RR^1R^2CCR^1R^2F$, wherein the reaction temperature is from about $-60°$ C. to about $-10°$ C., provided that total number of carbon atoms in $R^1R^2C=CR^1R^2$ is 5 or less.

9 Claims, No Drawings

US 8,247,625 B2

CATALYTIC ADDITION OF HYDROFLUOROCARBONS TO FLUOROOLEFINS

BACKGROUND OF THE INVENTION

1. Field of the Disclosure

The present disclosure relates in general to processes for manufacturing halogenated alkanes. More particularly, the present disclosure relates to the processes using $SbF_5$ catalyzed addition of hydrofluorocarbons across the carbon-carbon double bond of fluoroolefins.

2. Description of Related Art

Processes for the addition of hydrofluorocarbons to fluoroolefins using $SbF_5$ as a catalyst have been described in U.S. Pat. No. 6,184,426.

Halogenated compounds, especially fluorinated compounds, such as fluorocarbons and hydrofluorocarbons, have been widely used in the industry as refrigerants, solvents, cleaning agents, foam expansion agents, aerosol propellants, heat transfer media, dielectrics, fire extinguishing agents, sterilants and power cycle working fluids, et al. However, the side reactions from the processes used to manufacture these halogenated compounds produce significant amounts of unwanted by-products. These byproducts include perfluorocarbons and other chemicals that may have significant Global Warming Potential (GWP), or polymers that can fouling of the reactor and equipment, increasing maintenance costs.

Thus, there is a need for new manufacturing processes for the production of halogenated compounds.

SUMMARY OF THE INVENTION

A process has been provided for making $RR^1R^2CCR^1R^2F$ wherein R is selected from the group consisting of $CH_3$, $CH_2F$, $C_2H_4F$, and $F(CF_2)_nCH_2CH_2$ where n is an integer from 1 to 10, each $R^1$ is independently selected from the group consisting of H, Cl, F and $CF_3$, and each $R^2$ is independently selected from the group consisting of H, F and $CF_3$. The process comprises reacting RF with $R^1R^2C=CR^1R^2$ in the presence of $SbF_5$ to produce a product mixture comprising $RR^1R^2CCR^1R^2F$, wherein the reaction temperature is from about −60° C. to about −10° C., provided that total number of carbon atoms in $R^1R^2C=CR^1R^2$ is 5 or less.

The foregoing general description and the following detailed description are exemplary and explanatory only and are not restrictive of the invention, as defined in the appended claims.

DETAILED DESCRIPTION OF THE INVENTION

Before addressing details of embodiments described below, some terms are defined or clarified.

The term "perfluorocarbons" is intended to mean chemical compounds composing only of C and F. Perfluorocarbons include both straight chain and branched-chain compounds. Perfluorocarbons also include cyclic compounds.

The term "perfluoroethers" is intended to mean chemical compounds having ether bonds and composing only of C, O and F. Perfluoroethers include both straight chain and branched-chain compounds. Perfluoroethers also include cyclic compounds.

The term "perfluoro tertiary amines" is intended to mean tertiary amines wherein all the hydrogens have been substituted by fluorines.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

A process has been provided for making $RR^1R^2CCR^1R^2F$ wherein R is selected from the group consisting of $CH_3$, $CH_2F$, $C_2H_4F$, and $F(CF_2)_nCH_2CH_2$ where n is an integer from 1 to 10, each $R^1$ is independently selected from the group consisting of H, Cl, F and $CF_3$ and each $R^2$ is independently selected from the group consisting of H, F and $CF_3$ (for example,). As used herein, "independently selected from" means that for a given product or fluoroolefin, the R1 groups need not be identical, and the R2 groups need not be identical. For example, of the two $R^1$ groups, one may be H and the other may be $CF_3$, and of the two $R^2$ groups present in the molecule, one may be H and the other $CF_3$.

The process comprises reacting RF with a fluoroolefin, $R^1R^2C=CR^1R^2$ in the presence of $SbF_5$ to produce a product mixture comprising $RR^1R^2CCR^1R^2F$, wherein the reaction temperature is from about −60° C. to about −10° C. In one embodiment of the invention, the total number carbon atoms in $R^1R^2C=CR^1R^2$ is 5 or less. Fluoroolefins useful for the practice of this invention are commercially available from a variety of sources, or can be produced using the process disclosed in US Publication No. 2006/0106263 A1, the complete disclosure of which is incorporated herein by reference, or related U.S. application Ser. No. 11/264,183 the complete disclosure of which is also incorporated herein by reference.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

Examples of RF which can be used in the process for making $RR^1R^2CCR^1R^2F$ include $CH_3F$, $CH_2F_2$ and $CH_3CHF_2$.

Examples of $R^1R^2C=CR^1R^2$ which can be used in the process for making $RR^1R^2CCR^1R^2F$ include $CF_2=CF_2$, $CF_3CF=CF_2$, $CClF=CF_2$, $CClF=CClF$, $CHF=CF_2$, $CH_2=CF_2$, $CF_3CH=CF_2$, and $CHF=CFCF_3$.

$SbF_5$ is commercially available from Galaxy Chemicals LLC. (Claremore, Okla., U.S.A.).

The molar ratio of RF to $R^1R^2C=CR^1R^2$ fed to the reactor is at least 1:1. In one embodiment of the invention, the molar ratio of RF to $R^1R^2C=CR^1R^2$ fed to the reactor is greater than 1.1:1, particularly at least 2:1. In another embodiment of the invention, the molar ratio of RF to $R^1R^2C=CR^1R^2$ fed to the reactor is at least 3:1.

Optionally, solvents may be employed in the reaction process. In one embodiment of the invention, RF is also used as a solvent. In another embodiment of the invention, the solvent is an inert chemical compound that does not react with other chemical compounds or catalysts during the reaction. Suitable inert solvents may be selected from the group consisting of $R^3R^4R^5CCR^4R^5F$, perfluorocarbons, perfluoroethers and perfluoro tertiary amines, wherein $R^3$ is selected from the group consisting of $CH_3$, $CH_2F$, $C_2H_4F$, and $F(CF_2)_m CH_2CH_2$ where m is an integer from 1 to 10, each $R^4$ is independently selected from the group consisting of H, Cl, F and $CF_3$, and each $R^5$ is independently selected from the group consisting of H, F and $CF_3$.

In one embodiment of this invention, the inert solvent is the same chemical compound as the product $RR^1R^2CCR^1R^2F$, i.e. $R^3=R$, $R^4=R^1$, $R^5=R^2$.

In another embodiment of this invention, RF and $SbF_5$ are pre-mixed before contacting with $R^1R^2C=CR^1R^2$.

In another embodiment of this invention, at least part of RF, $SbF_5$, and at least one inert solvent are pre-mixed before contacting with $R^1R^2C=CR^1R^2$.

In another embodiment of this invention, at least part of RF, $SbF_5$, and at least one inert solvent are pre-mixed before contacting with $R^1R^2C=CR^1R^2$. In such a pre-mixed mixture, the molar ratio of RF to the total amount of inert solvent is less than 95:5.

In another embodiment of this invention, at least part of RF, $SbF_5$, and at least one inert solvent are pre-mixed before contacting with $R^1R^2C=CR^1R^2$. In such a pre-mixed mixture, the molar ratio of RF to the total amount of inert solvent is less than 70:30.

In another embodiment of this invention, no HF is fed independently to the reactor. It is understood that $SbF_5$ and other chemical compounds fed to the reactor, such as RF and $R^1R^2C=CR^1R^2$, may contain small amounts of HF as an impurity. HF may also be generated by the side-reactions, e.g. $SbF_5$ reacting with moisture in solvents or other chemical compounds. However, HF should be generally avoided.

The temperature employed in the reaction process typically ranges from about $-60°$ C. to $-10°$ C. In one embodiment of the invention, the temperature employed in the reaction process ranges from about $-50°$ C. to $-10°$ C. In another embodiment of the invention, the temperature employed in the reaction process ranges from about $-40°$ C. to $-10°$ C. In another embodiment of the invention, the temperature employed in the reaction process ranges from about $-35°$ C. to $-10°$ C.

It has been found that a relatively large amount of $CF_3CF_3$ was generated in the reaction process when the temperature was higher than about $-10°$ C. Without wishing to be bound by the theory, it is believed that $CF_3CF_3$ is produced by the reaction between $CF_2=CF_2$ and $SbF_5$. This reaction consumes $SbF_5$ and should be minimized.

Reaction time is not critical and typically ranges from about 5 seconds to about 10 hours. In one embodiment of the invention, the reaction time ranges from about 1 hour to about 5 hours.

The pressure employed in the reaction is not critical. Typically, the reaction is conducted under autogenous pressure. However, the pressure should not exceed 300 psig when $R^1R^2C=CR^1R^2$ is tetrafluoroethylene.

The product $RR^1R^2CCR^1R^2F$ can be recovered from the product mixtures by distillation, e.g. fractional distillation.

The reactors, distillation columns, and their associated feed lines, effluent lines, and associated units used in applying the processes of embodiments of this invention should be constructed of materials resistant to corrosion. Typical materials of construction include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

Since $SbF_5$ is water sensitive, the reaction should take place under anhydrous or near anhydrous conditions, i.e. the chemical compounds fed to the reactor and reactor itself and associated feed lines should be dry.

EXAMPLES

The concepts described herein will be further described in the following examples, which do not limit the scope of the invention described in the claims.

Legend

| | |
|---|---|
| HFC-32 is $CH_2F_2$ | HFC-236cb is $CF_3CF_2CH_2F$ |
| TFE is $CF_2=CF_2$ | PFC-116 is $CF_3CF_3$ |
| PTFE is polytetrafluoroethylene | HFC-245cb is $CF_3CF_2CH_3$ |
| HFC-125 is $CF_3CF_2H$ | |

Example 1

Example 1 demonstrates that HFC-32 and TFE react smoothly at temperatures below $-10°$ C. and using $SbF_5$ as the catalyst to produce HFC-236cb when HFC-32 and $SbF_5$ are pre-mixed. Little PFC-116 is produced.

A 1000 ml Hastelloy autoclave reactor was charged with antimony pentafluoride (87.5 g, 0.40 mol). The reactor was cooled down to $-16°$ C. and evacuated. The reactor was then charged with HFC-32 (390 g, 7.5 mol). The mixture was stirred. Then HFC-32/TFE (1.1:1 molar ratio) mixture was fed into the reactor at 400 ml/min while the stirring continued. The temperature of the reactor was controlled between $-10°$ to 15° C. After a total of 390 g of HFC-32/TFE (2.48 mole of TFE and 2.73 mole of HFC-32) mixture had been added, the reaction mixture was stirred at $-12°$ C. for 1 hr. The reaction product mixture was collected in a cold trap. No PTFE polymer was found in the reactor after the reaction stopped. At the end of the reaction, both vapor phase and liquid phase of the product mixture in the reactor were analyzed by GC-MS. The analytical results are given in units of GC area % in Table 1 and Table 2 below. Small amounts of other products, not included in Table 1 and Table 2 were also present. The vapor phase sample was taken at $-16.3°$ C. and 48.3 psig from 300 ml vapor space in the reactor. It was calculated according to the gas law that about $2.8\times10^{-4}$ moles of PFC-116 was generated in the reaction.

TABLE 1

| (Vapor Phase) | | | |
|---|---|---|---|
| HFC-32 | PFC-116 | HFC-236cb | air |
| 59.5 | 2.4 | 26.3 | 10.9 |

TABLE 2

| (Liquid Phase) | | |
|---|---|---|
| HFC-32 | HFC-245cb | HFC-236cb |
| 8.0 | 1.8 | 89.9 |

Example 2

Example 2 demonstrates that HFC-236cb can be used as a solvent.

A 1000 ml Hastelloy autoclave reactor was charged with antimony pentafluoride (130 g, 0.55 mol). The reactor was cooled down to −16° C. and evacuated. The reactor was then charged with HFC-32 (170 g, 3.27 mol) and 236cb (258 g, 1.70 mol). The mixture was stirred. Then HFC-32/TFE (1.1:1 molar ratio) mixture was fed into the reactor at 400 ml/min while the stirring continued. The temperature of the reactor was controlled between −10° to −15° C. After a total of 480 g of HFC-32/TFE (3.05 mole of TFE and 3.36 mole of HFC-32) mixture had been added, the reaction mixture was stirred at −12° C. for 1 hr. The reaction product mixture was collected in a cold trap. No PTFE polymer was found in the reactor after the reaction stopped. At the end of the reaction, both vapor phase and liquid phase of the product mixture in the reactor were analyzed by GC-MS. The analytical results are given in units of GC area % in Table 3 and Table 4 below. Small amounts of other products, not included in Table 3 and Table 4 were also present. The vapor phase sample was taken at −10° C. and 42 psig from 360 ml vapor space in the reactor. It was calculated according to the gas law that about $1.6 \times 10^{-4}$ moles of PFC-116 was generated in the reaction.

TABLE 3

| (Vapor Phase) | | | |
|---|---|---|---|
| HFC-32 | PFC-116 | HFC-236cb | air |
| 68.9 | 3.5 | 28.8 | 17.7 |

TABLE 4

| (Liquid Phase) | |
|---|---|
| HFC-32 | HFC-236cb |
| 6.6 | 92.8 |

Example 3 (Comparative)

Example 3 demonstrates that when HFC-32 and TFE are co-fed as a 1:1 molar ratio mixture without pre-mixing of HFC-32 with the catalyst, PTFE will be produced and a significant amount of TFE will remainas unreacted.

A 1000 ml Hastelloy autoclave reactor was charged with antimony pentafluoride (106 g, 0.49 mol). The reactor was cooled down to −16° C. and evacuated. The reactor was then charged with 236cb (353 g, 2.32 mol). The mixture was stirred.

Then HFC-32/TFE (1:1 molar ratio) mixture was fed into the reactor at 800 ml/min while the stirring continued. The temperature of the reactor was controlled between −9° to −4° C. When a total of 130 g of HFC-32/TFE (0.85 mole of TFE and 0.85 mole of HFC-32) mixture was added, the pressure in the reactor rose from 17.1 psig to 90 psig. Without wishing to be bound by the theory, it is believed that the catalyst was significantly deactivated and the reaction significantly slowed down. The reaction product mixture was collected in a cold trap. PTFE polymer was found coated on surfaces of cooling coils in the reactor. The reaction product mixture was analyzed by GC-MS. The analytical results are given in units of GC area % in Table 5 below. Small amounts of other products, not included in Table 5 were also present.

TABLE 5

| HFC-32 | TFE | PFC-116 | HFC-125 | HFC-236cb |
|---|---|---|---|---|
| 11.4 | 13.4 | 5.9 | 0.1 | 68.5 |

Example 4 (Comparative)

Example 4 demonstrates that when the reaction temperature is at about −5° C., a relatively large amount of $CF_3CF_3$ is produced.

A 1000 ml Hastelloy autoclave reactor was charged with antimony pentafluoride (130 g, 0.55 mol). The reactor was cooled down to −16° C. and evacuated. The reactor was then charged with HFC-32 (154.8 g, 2.98 mol) and 236cb (216 g, 1.42 mol). The mixture was stirred. Then HFC-32/TFE (1.1:1 molar ratio) mixture was fed into the reactor at 400 ml/min while the stirring continued. The temperature of the reactor was controlled between −7° to −3° C. After a total of 185 g of HFC-32/TFE (1.18 mole of TFE and 1.30 mole of HFC-32) mixture had been added, the reaction mixture was stirred at −5° C. for 1 hr. The reaction product mixture was collected in a cold trap. No PTFE polymer was found in the reactor after the reaction stopped. At the end of the reaction, both vapor phase and liquid phase of the product mixture in the reactor were analyzed by GC-MS. The analytical results are given in units of GC area % in Table 6 and Table 7 below. Small amounts of other products, not included in Table 6 and Table 7 were also present. The vapor phase sample was taken at −7° C. and 41 psig from 600 ml vapor space in the reactor. It was calculated according to the gas law that about $3.6 \times 10^{-3}$ moles of PFC-116 was generated in the reaction.

TABLE 6

| (Vapor Phase) | | | |
|---|---|---|---|
| HFC-32 | PFC-116 | HFC-236cb | air |
| 45.1 | 4.9 | 32.1 | 16.5 |

TABLE 7

| (Liquid Phase) | |
|---|---|
| HFC-32 | HFC-236cb |
| 5.8 | 92.8 |

Example 5 (Comparative)

Example 5 demonstrates that no reaction occurs between $CH_2F_2$ and $CF_2=CF_2$ when $TaF_5$ is used as a catalyst under conditions similar to Examples 2 and 3 above.

A 400 ml Hastelloy C shaker tube was charged with TaF$_5$ (8 g, 0.029 mol). The tube was cooled down to −30° C. and evacuated. The tube was then charged with CH$_2$F$_2$ (26 g, 0.5 mol) and CF$_2$=CF$_2$ (40 g, 0.4 mol).

Then the reaction mixture was warmed up to 100° C. and stirred at 100° C. for 8 hours. No reaction was detected.

Example 6

Example 6 demonstrates that when the reaction temperature is at about 0° C., a relatively large amount of CF$_3$CF$_3$ is produced and PTFE is also produced.

A 1000 ml Hastelloy autoclave reactor was charged with antimony pentafluoride (71 g, 0.33 mol). The reactor was cooled down to −30° C. and evacuated. The reactor was then charged with HFC-32 (164, 3.15 mol) and 236cb (200 g, 1.32 mol). The mixture was stirred and then warmed up to 0° C. Then at 0° C. HFC-32/TFE (1.1:1 molar ratio) mixture was fed into the reactor at 400 ml/min while the stirring continued. The temperature of the reactor was controlled between −2° C. to 0° C. After a total of 215 g of HFC-32/TFE (1.37 mole of TFE and 1.50 mole of HFC-32) mixture had been added, the feed was stopped. Then the reaction mixture was stirred at 0° C. for 1 hr. The reaction product mixture was collected in a cold trap. PTFE polymer was found in the reactor after the reaction stopped. At the end of the reaction, vapor phase of the product mixture in the reactor were analyzed by GC-MS. The analytical results are given in units of GC-MS area % in Table 8 below. Small amounts of other products, not included in Table 8 were also present. The vapor phase sample was taken at 0° C. and 64 psig from 600 ml vapor space in the reactor. It was calculated according to the external standard and gas law that about 2.45×10$^{-3}$ moles of PFC-116 was generated in the reaction. That means about 0.18% of fed TFE was fluorinated to PFC-116.

TABLE 8

| (Vapor Phase) | | |
|---|---|---|
| HFC-32 | PFC-116 | HFC-236cb |
| 45.01 | 9.93 | 44.61 |

Example 7

Example 7 demonstrates that when the reaction temperature is at about −30° C., a relatively small amount of CF$_3$CF$_3$ is produced.

A 1000 ml Hastelloy autoclave reactor was charged with antimony pentafluoride (69 g, 0.32 mol). The reactor was cooled down to −30° C. and evacuated. The reactor was then charged with HFC-32 (178 g, 3.42 mol) and 236cb (201 g, 1.32 mol). The mixture was stirred at −30° C. Then at −30° C. HFC-32/TFE (1.1:1 molar ratio) mixture was fed into the reactor at 400 ml/min while the stirring continued. The temperature of the reactor was controlled between −27° C. to −32° C. After a total of 260 g of HFC-32/TFE (1.65 mole of TFE and 1.82 mole of HFC-32) mixture had been added, the reaction mixture was stirred at −30° C. for 1 hr. The reaction product mixture was collected in a cold trap. No PTFE polymer was found in the reactor after the reaction stopped. At the end of the reaction, vapor phase of the product mixture in the reactor were analyzed by GC-MS. The analytical results are given in units of GC-MS area % in Table 9 below. Small amounts of other products, not included in Table 9 were also present. The vapor phase sample was taken at 0° C. and 64 psig from 600 ml vapor space in the reactor. It was calculated according to external standard and the gas law that about 4.9×10$^{-4}$ moles of PFC-116 was generated in the reaction. That means about 0.024% of fed TFE was fluorinated to PFC-116.

TABLE 9

| (Vapor Phase) | | | |
|---|---|---|---|
| HFC-32 | PFC-116 | HFC-236cb | air |
| 44.685 | 4.35 | 25.6 | 12.98 |

Example 8

Example 8 demonstrates that when HFC-32/HFC-236cb (70:30 molar ratio) pre-mixed mixture was used, only a trace amount of tar was produced.

A 1000 ml Hastelloy autoclave reactor was charged with antimony pentafluoride (71 g, 0.33 mol). The reactor was cooled down to −30° C. and evacuated. The reactor was then charged with HFC-32 (164 g, 3.15 mol) and HFC-236cb (200 g, 1.32 mol). The mixture was stirred and then warmed up to −10° C. Then at −10° C. HFC-32/TFE (1.1:1 molar ratio) mixture was fed into the reactor at 400 ml/min while the stirring continued. The temperature of the reactor was controlled between −12° C. to −9° C. After a total of 260 g of HFC-32/TFE (1.656 mole of TFE and 1.82 mole of HFC-32) mixture had been added, the feed was stopped. Then the reaction mixture was stirred at −10° C. for 1 hr. The reaction product mixture was collected in a cold trap. 600 g of water was pumped into the reactor to digest the catalyst. Very little of tar was found in the reactor in digested catalyst. At the end of the reaction, both vapor phase and liquid of the product mixture in the reactor were analyzed by GC-MS. The analytical results are given in units of GC-MS area % in Tables 10 and 11 below. Small amounts of other products not included in Tables 10 and 11 were also present. The vapor phase sample was taken at −10° C. and 41 psig from vapor space in the reactor.

TABLE 10

| (Vapor Phase) | | | |
|---|---|---|---|
| HFC-32 | PFC-116 | HFC-236cb | air |
| 45.36 | 7.74 | 38.09 | 7.91 |

TABLE 11

| (Liquid Phase) | | | |
|---|---|---|---|
| HFC-32 | PFC-116 | HFC-236cb | air |
| 13.76 | 0.216 | 84.07 | 1.74 |

Example 9

Example 9 demonstrates that when HFC-32 was fed to the reactor without inert solvents, a relatively large amount of tar was produced.

A 1000 ml Hastelloy autoclave reactor was charged with antimony pentafluoride (100 g, 0.46 mol). The reactor was cooled down to −30° C. and evacuated. The reactor was then charged with HFC-32 (450 g, 8.65 mol). The mixture was stirred and then warmed up to −10° C. Then at −10° C. TFE was fed into the reactor at 200 ml/min while the stirring continued.

The temperature of the reactor was controlled between −12° C. to −9° C.

After a total of 180 g of TFE (1.8 mole of TFE) had been added, the feed was stopped. Then the reaction mixture was stirred at −10° C. for 1 hr. The reaction product mixture was collected in a cold trap. 600 g of water was pumped into the reactor to digest the catalyst. A large amount of tar was found in the reactor in digested catalyst. At the end of the reaction, both vapor phase and liquid of the product mixture in the reactor were analyzed by GC-MS. The analytical results are given in units of GC-MS area % in Table 12 and 13 below. Small amounts of other products, not included in Table 12 and 13, were also present. The vapor phase sample was taken at −10° C. and 63 psig from vapor space in the reactor.

TABLE 12

(Vapor Phase)

| HFC-32 | PFC-116 | HFC-236cb | air |
|---|---|---|---|
| 70.06 | 1.869 | 20.10 | 5.36 |

TABLE 13

(Liquid Phase)

| HFC-32 | HFC-245cb | HFC-236cb | air |
|---|---|---|---|
| 31.47 | 2.55 | 64.40 | 1.19 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for making $RR^1R^2CCR^1R^2F$ wherein R is selected from the group consisting of $CH_3$, $CH_2F$, $C_2H_4F$, and $F(CF_2)_nCH_2CH_2$ where n is an integer from 1 to 10, each $R^1$ is independently selected from the group consisting of H, Cl, F and $CF_3$, and each $R^2$ is independently selected from the group consisting of H, F and $CF_3$, comprising: reacting RF with $R^1R^2C\!\!=\!\!CR^1R^2$ in the presence of $SbF_5$ to produce a product mixture comprising $RR^1R^2CCR^1R^2F$, wherein the reaction temperature is from about −60° C. to below −10° C., provided that total number of carbon atoms in $R^1R^2C\!\!=\!\!CR^1R^2$ is 5 or less.

2. The process of claim 1 wherein no HF is fed to the reactor.

3. The process of claim 1 further comprising: pre-mixing the $SbF_5$ and the RF.

4. The process of claim 1 wherein at least one inert solvent is also present, wherein said at least one inert solvent is selected from the group consisting of $R^3R^4R^5CCR^4R^5F$, perfluorocarbons, perfluoroethers and perfluoro tertiary amines, wherein $R^3$ is selected from the group consisting of $CH_3$, $CH_2F$, $C_2H_4F$, and $F(CF_2)_mCH_2CH_2$ where m is an integer from 1 to 10, each $R^4$ is independently selected from the group consisting of H, Cl, F and $CF_3$, and each $R^5$ is independently selected from the group consisting of H, F and $CF_3$.

5. The process of claim 4 further comprising: pre-mixing the $SbF_5$ and at least part of the RF with said at least one inert solvent.

6. The process of claim 5 wherein the molar ratio of said at least part of the RF to the total amount of said at least one inert solvent in the pre-mixed mixture is less than 95:5.

7. The process of claim 6 wherein the molar ratio of said at least part of the RF to the total amount of said at least one inert solvent in the pre-mixed mixture is less than 70:30.

8. The process of claim 5 wherein $R^3\!\!=\!\!R$, $R^4\!\!=\!\!R^1$, $R^5\!\!=\!\!R^2$.

9. The process of claim 8 wherein R is $CH_2F$, $R^1\!\!=\!\!R^2\!\!=\!\!F$, and said at least one inert solvent is 1,1,1,2,2,3-hexafluoropropane.

* * * * *